United States Patent
Chipman

(10) Patent No.: US 7,612,880 B2
(45) Date of Patent: Nov. 3, 2009

(54) ADVANCED POLARIZATION IMAGING METHOD, APPARATUS, AND COMPUTER PROGRAM PRODUCT FOR RETINAL IMAGING, LIQUID CRYSTAL TESTING, ACTIVE REMOTE SENSING, AND OTHER APPLICATIONS

(75) Inventor: Russell Chipman, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 10/567,104

(22) PCT Filed: Aug. 3, 2004

(86) PCT No.: PCT/US2004/024477

§ 371 (c)(1),
(2), (4) Date: Nov. 10, 2006

(87) PCT Pub. No.: WO2005/017826

PCT Pub. Date: Feb. 24, 2005

(65) Prior Publication Data

US 2007/0146632 A1    Jun. 28, 2007

Related U.S. Application Data

(60) Provisional application No. 60/492,805, filed on Aug. 6, 2003.

(51) Int. Cl.
*G01J 4/00*    (2006.01)

(52) U.S. Cl. .......................... 356/364; 356/365; 356/369
(58) Field of Classification Search ........... 356/364–369
See application file for complete search history.

(56) References Cited

U.S. PATENT DOCUMENTS

| 5,519,493 | A | | 5/1996 | Reiley |
| 5,603,710 | A | * | 2/1997 | Easley et al. ............... 606/15 |
| 5,793,480 | A | | 8/1998 | Lacey et al. |
| 5,936,734 | A | * | 8/1999 | Johs et al. ................ 356/364 |
| 6,384,916 | B1 | | 5/2002 | Furtak |
| 6,927,888 | B2 | * | 8/2005 | Garcia et al. ............. 356/369 |
| 7,287,855 | B2 | * | 10/2007 | Zhou et al. ............... 356/365 |

* cited by examiner

*Primary Examiner*—Gregory J Toatley, Jr.
*Assistant Examiner*—Iyabo S Alli
(74) *Attorney, Agent, or Firm*—Oblon, Spivak, McClelland, Maier & Neustadt, P.C.

(57) ABSTRACT

A method, apparatus, and computer program product for identifying features in a sample by analyzing Mueller matrices to calculate an average degree of polarization, a weighted average degree of polarization, a degree of polarization map, a degree of polarization surface. Also, a method, apparatus, and computer program product for identifying features in a sample by analyzing Mueller matrices to calculate depolarization relative to a retardance axis and/or a diattentuation axis, and to calculate a ratio of diattenuation to polarizance or ratios of row and column magnitudes. Also, a method for retinal polarimetry, including a non-depolarizing light tube configured for insertion into the eye.

19 Claims, 8 Drawing Sheets

ADVANCED POLARIZATION IMAGING METHOD, APPARATUS, AND COMPUTER PROGRAM PRODUCT FOR RETINAL IMAGING, LIQUID CRYSTAL TESTING, ACTIVE REMOTE SENSING, AND OTHER APPLICATIONS

CROSS REFERENCE TO RELATED PATENT DOCUMENTS

This application contains subject matter related to that disclosed in the following co-pending provisional patent application, the contents of which are incorporated herein by reference: U.S. Patent Application Ser. No. 60/492,805 filed on Aug. 6, 2003.

BACKGROUND OF THE INVENTION

1. Field of Invention

The invention describes a method utilizing actively illuminated imaging polarimetry for identifying a feature or features in an object through evaluation of how the object scrambles different incident fully polarized states into partially polarized states. Such a reduction in the degree of polarization of the light can be due to variations in the object below the resolution imaging system.

2. Description of the Background Art

An active polarization image of an object, usually in the form of a Mueller matrix image, contains pixel-by-pixel information on the intensity, the retardance, and the diattenuation (partial polarization) of the object at the spatial resolution of the camera or imaging system. When the proper measurements are performed and analyzed by the means of the present invention, information is obtained on the variations of the polarization properties within a pixel. Although imaging information regarding the spatial location of features within a pixel cannot be obtained below the resolution of the instrument, useful information is obtained on the variations of structures, the types of those structures, their orientations, and overall order when these structures modulate polarization spatially. The exploitation of these polarization parameters is useful in medical diagnostics (e.g., retinal disease diagnostics), crystal analysis, surveillance and many other applications.

The eye is subject to a number of pathologies and disease states which, if unchecked, lead to the impairment and possible loss of vision. Non-invasive optical methods are a preferential method for assessing the status of the eye because of ease of measurement. But the common eye diseases, including glaucoma, diabetic retinopathy, and Age-related Macular Degeneration (AMD) do not produce easily detectable changes during their early stages because many ocular structures are transparent and because others are obscured by opaque tissues. Improved optical ophthalmic diagnostics hold the promise of detecting ocular disease earlier and of quantifying the state of the disease more accurately so that its progression can be tracked and the effectiveness of treatments such as drug treatments can be evaluated.

One principal ophthalmic diagnostic is fundus imaging which takes a conventional image of the inside of the eye. To produce an image requires a contrast mechanism, in the case of the eye a distribution of chromophores. But the eye is nearly transparent from the cornea until the retinal pigment epithelium is encountered. In the back of the eye the dominant chromophores are hemoglobin in the retinal blood vessels and melanin in the retinal pigment epithelium (RPE). Thus there are not that many strong contrast mechanisms for imaging to exploit. Fundus imaging can detect neovascularization associated with diabetic retinopathy and the cupping of the optic nerve head associated with advanced glaucoma. But fundus imaging cannot detect AMD, early stage glaucoma, or the precursors to diabetic retinopathy.

Another successful ophthalmic imaging diagnostic is optical coherence tomography (OCT) which constructs a three dimensional image of retinal tissue by scanning a broad band point source while rapidly adjusting an interferometric delay line. OCT reveals details which fundus imaging cannot include the nerve fiber layer and structures deeper in the retina including the RPE, Bruchs membrane, and the choroid. Being interferometric, OCT images are speckle patterns making quantitative image analysis of small features very difficult. OCT does not measure the polarization of transparent birefringent structures or depolarization and thus misses much useful information on the retina.

To obtain additional information on the retina and other ocular structures polarization can be used to induce contrast in transparent tissues or to modify the contrast in tissues with chromophores. Polarization provides an additional set of contrast mechanisms through the three basic polarization properties, retardance, diattenuation, and depolarization. All light/matter polarization effects can be classified into these three groups.

The largest polarization effects in the eye are associated with retardance, the phase delay between polarization states which accumulates when light propagates through birefringent materials. In the eye large retardance is associated with the cornea and the nerve fiber layer and small but nonzero retardance with all other transparent tissues.

The present invention addresses methods of measuring other polarization effects and applying these methods to retinal imaging and other problems involving active polarimetric imaging. To prepare for this complex discussion of depolarization imaging, first the present ophthalmic polarization measuring technologies will be reviewed and their limitations considered, including the techniques of nerve fiber layer (NFL) retardance imaging and Mueller matrix imaging.

The NFL layer consists of retinal ganglion cell axons which are arranged into bundles of parallel fibers. This assembly of fibers is modeled as arrays of parallel, weakly reflecting nonabsorbing, dielectric cylinders embedded in a medium of slightly lower refractive index. The cylinder array model has been used to predict that the reflection of the NFL should be proportional to thickness, and that the backscattering reflection should be into a cone. The model has also been used to predict that the NFL possesses 'linear form birefringence' and behaves as a positive uniaxial crystal with optic axis parallel to the axis of the fibers. These predictions have been experimentally verified with some success; in particular, retardance magnitude has been shown to correlate well with NFL thickness. With more careful histology of retinal samples, it has been shown that a number of coaxial quasicylindrical structures of various diameters are present. As a result, the array model has been extended to include both thin cylinders (diameter ~1/10 of a wavelength) and thick cylinders (diameter ~1 wavelength). Considerable success has been achieved in using this model to explain experimentally obtained polarization measurements. Reported results indicate that the retina is a linear retarder, with retardance dependent on thickness; and that there is weak diattenuation and little depolarization on reflection. Reported retardance values are in the range of 2-4nm for NFL thickness of ~15μm, corresponding to approximately 0.2nm/μm.

Several obstacles exist to determining retinal polarization by direct measurement. Probably the most significant is that the polarization state of light entering the eye may be modified by other ocular structures, such as the cornea, crystalline lens, and vitreous. The vitreous and lens appear to have no significant polarization effect, but the cornea can have very substantial effect. Studies in humans suggest that the cornea is a linear retarder with slow axis pointing nasally downward, with the retardance magnitude increasing radially. The orientation and magnitude of the retardance has been shown to vary significantly between individuals, with double-pass retardances of 0-250 nm reported. Some researchers have attempted to avoid this problem by excising the anterior segment of the eye, and others have attempted to compensate for the corneal retardance by inserting a fixed or variable compensatory retarder in the measurement path.

A polarimeter for measurements of the NFL is commercially available from Laser Diagnostics, San Diego, Calif. and is called the GDx Retinal Polarimeter. The GDx is approved by the FDA for the diagnosis of glaucoma. The GDx is marketed as an instrument which assists in early glaucoma detection. The GDx is described in U.S. Pat. No. 6,704,106 to Anderson.

FIG. 4 in this patent is a diagram of the optical layout of the GDx and explains how the GDx acquires polarization information. A 780 nm laser diode is polarized and coupled into the main optical axis by a non-polarizing or nearly non-polarizing beam splitter. The polarization state is modulated by a rotating half wave linear retarder. A two axis scanner raster scans the beam. The light passes through an optional corneal polarization compensator which is only present is some models. A variable focus lens directs the light into the eye where the polarized light interacts with the tissues of the eye, in particular the cornea and retinal nerve fiber layer. The variable focus lens is adjusted to focus to a small spot of light on the retina. The raster scanned beam reflects and scatters from the back of the eye and the returned light constitutes an image. After each image the half wave linear retarder is rotated to change the generated polarization state and the analyzed polarization state. The light scattered from the eye passes back through the rotating half wave linear retarder and is divided at the non-polarizing beam splitter. The half of the beam reflected back toward the source is lost. The transmitted fraction enters a polarizing beam splitter where the s- and p-polarized components are split and detected by separate detectors. One detectors signal corresponds to the co-polarized signal, it is polarized parallel to the illuminating beam and is the portion of the light whose polarization was not changed. The other detector measures the cross-polarized signal, that component whose polarization state was changed. The GDx illuminates the eye with twenty linearly polarized beams each oriented 18° from the next generated by a rotating half wave linear retarder.

Thus, with the standard GDx, 20 images are acquired, ten co-polarized and ten cross-polarized. Pixel by pixel, from a sinusoidal fit to these intensity values, the linear retardance and the retardance orientation are determined which when combined constitute a retardance image of the eye. The GDx compensates for the retardance of the cornea to produce a retardance image of the retina from which the thickness of the nerve fiber layer is determined. A normal retardance distribution indicates NFL health. A thin NFL is an indication of glaucoma. A series of measurements can document the progressive thinning and estimate the rate of glaucoma progression.

The GDx as produced by Laser Diagnostics is an incomplete polarimeter. The GDx cannot measure a complete Mueller matrix, cannot measure diattenuation, and cannot measure any depolarization parameters as the present invention can.

The GDx is designed to measure linear retardance, which correlates with the thickness and health of the NFL. The GDx does not measure the other polarization properties: diattenuation and depolarization. Thus, the GDx device does not provide a full set of depolarization images of the retina and, therefore, does not provide a complete set of information about the deeper layers of the retina, lesions associated with neovascularization and basal and basal laminar deposits.

A simplified version of FIG. 4 of U.S. Pat. No. 6,704,106 is shown in FIG. 1, where a laser emits light through a polarizer onto a non-polarizing beam splitter. One part of the light beam is reflected to the eye via a rotating half-wave retarder and an objective lens. Another part of the light beam is reflected toward a polarizing beam splitter. The polarizing beam splitter reflects co-polarized light to one photodetector and, optionally, cross-polarized light to another photodetector. Light reflected from the eye also passes through the two beam splitters to the photodetectors.

The aforementioned limitations are partially addressed by conventional Mueller matrix imaging of ocular tissues. However, before describing these conventional methods and systems for Mueller matrix imaging of ocular tissues, a background discussion of Mueller matrices is presented.

Depolarization can be calculated by comparing the input and output Degree of Polarization (DoP) of Stokes vectors. A more general method is via algorithms which operate on Mueller matrices. This is the subject of the present invention. These methods are more general because different polarization states are depolarized by different amounts, and these variations occur in many different ways, i.e. with different degrees of freedom. Before presenting the present inventions several quantities regarding Mueller matrices need to be given precise definitions. The present invention is a set of new algorithms to exploit these depolarization variations described by the Mueller matrix to infer additional information on the structure and subpixel order of the sample.

Frequent reference is made here to the description of polarization states by Stokes vectors, their location on the Poincaré sphere, and the properties of Mueller matrices, all defined and extensively discussed in 3.1.6 and 3.2.1 of Brossseau (1998) and many other standard works on optical polarization. All fully polarized Stokes vectors can be described by their location on the Surface of the Poincaré sphere by the equation $$S[\theta, \phi] = \begin{bmatrix} 1 \\ \cos[2\theta]\cos[\phi] \\ \sin[2\theta]\cos[\phi] \\ \sin[\phi] \end{bmatrix} = \begin{bmatrix} S_0 \\ S_1 \\ S_3 \\ S_4 \end{bmatrix}. \quad (1)$$

where the parameter θ is the orientation of polarization ellipse major axis and φ is the latitude on the Poincaré sphere.

The Degree of Polarization (DoP) of a Stokes vector is defined as $$DoP[S] = \frac{\sqrt{S_1^2 + S_2^2 + S_3^2}}{S_0}. \quad (2)$$

When the DoP of the exiting beam is less than the DoP of the incident beam, then depolarization occurred. In particular when the incident beam is completely polarized (DoP=1) and the exiting beam has a DoP=a, where $0 \leq a \leq 1$, then the reduction in DoP, 1−a, indicates the depolarization that particular polarization state.

Two other Stokes vector parameters will be used later in the DoP maps. The orientation of the major axis of the polarization ellipse, $\theta$, is given by $$\theta = \frac{1}{2} \text{ArcTan}(S_2/S_1). \quad (3)$$

The Degree of Circular Polarization, DoCP, is $$DoCP[S] = \frac{S_3}{S_0}. \quad (4)$$

A linear interaction of incident light with a sample has its polarization transformations properties are described by a Mueller matrix, M, that relates the incident Stokes vector, $S_{incident}$, with the exiting Stokes vector, $S_{Exiting}$, by the relation $$S_{Exiting} = M \cdot S_{Incident} = \begin{bmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{bmatrix} \cdot \begin{bmatrix} S_0 \\ S_1 \\ S_2 \\ S_3 \end{bmatrix} = \begin{bmatrix} S'_0 \\ S'_1 \\ S'_2 \\ S'_3 \end{bmatrix}. \quad (5)$$

Those skilled in the optics understand that nonlinear interactions of light with samples, such as occur at higher light intensity levels are described by similar but more complex equations where a different Mueller matrix is necessary for each generated wavelength.

The exiting DoP for each possible incident Stokes vector is given by the equation $$DoP(M, S) = \frac{\sqrt{S'_1(M, S)^2 + S'_2(M, S)^2 + S'_3(M, S)^2}}{S'_0(M, S)}. \quad (6)$$

This equation contains information on all the possible depolarizations which an optical element or polarimetry sample performs at the wavelength, angle of incidence, aperture, and other optical beam parameters where the Mueller matrix was measured, calculated, or simulated.

Before discussing the more complex depolarization properties which are the subject of the invention, several conventional polarization properties associated with a Mueller matrix shall be defined in the exact mathematical form which will be used in the following algorithms including the following: diattenuation, diattenuation vector, polarizance, polarizance vector, retardance, and retardance vector. These comprise the basic nondepolarizing properties of a polarization transformation.

Diattenuation

Diattenuation is the property of polarizers and partial polarizers whereby the transmission is a function of the incident polarization state. Diattenuation is entirely described by the first row of the Mueller matrix by elements $m_{00}$, $m_{01}$, $m_{02}$, and $m_{03}$. The diattenuation (also "diattenuation magnitude"), D, is $$D = \frac{\sqrt{m_{01}^2 + m_{02}^2 + m_{03}^2}}{m_{00}} = \frac{T_{max} - T_{min}}{T_{max} + T_{min}}, \quad (7)$$

which describes the degree to which M is a partial polarizer, given by the maximum and minimum transmittance. Further these elements define two additional degrees of freedom on the Poincaré sphere, the diattenuation axis orientation and latitude as $$((2\theta)_{axis}, \phi_{axis}) = \quad (8)$$
$$\left( \text{ArcCos}\left[ \frac{m_{01}}{\sqrt{m_{01}^2 + m_{02}^2}} \right], \text{ArcSin}\left[ \frac{m_3}{\sqrt{m_{01}^2 + m_{02}^2 + m_{03}^2}} \right] \right).$$

The diattenuation axis passes through the incident polarization states of maximum transmittance, $S_{max}$, also called the Diattenuation Vector, $$S_{max} = (\sqrt{m_{01}^2 + m_{02}^2 + m_{03}^2}, m_{01}, m_{02}, m_{03}) \quad (9)$$

and the incident polarization state of minimum transmittance, $S_{min}$, $$S_{min} = (\sqrt{m_{01}^2 + m_{02}^2 + m_{03}^2}, -m_{01}, -m_{02}, -m_{03}) \quad (10)$$

Polarizance

Polarizance describes the ability of a polarization element to polarize unpolarized light. Polarizance, P, is entirely described by the first column of the Mueller matrix by elements $m_{00}$, $m_{10}$, $m_{20}$, and $m_{30}$, and is $$P = \frac{\sqrt{m_{10}^2 + m_{20}^2 + m_{30}^2}}{m_{00}}, \quad (11)$$

which is the degree of polarization of the exiting light when unpolarized light is incident on Mueller matrix, M. The Polarizance Vector, PV, is this exiting state, $$PV = (\sqrt{m_{10}^2 + m_{20}^2 + m_{30}^2}, m_{10}, m_{20}, m_{30}) \quad (12)$$

The Depolarization Index

A Mueller matrix which is not depolarizing is called a Non-depolarizing Mueller Matrix and satisfies the condition $$4M_{00}^2 = \sum_{i=0}^{3} \sum_{j=0}^{3} M_{i,j}^2. \quad (13)$$

This constraint was manipulated by Gil and Bernabeu in 1985 to obtain the Depolarization Index, DI, the only single number metric in common usage for characterizing the depolarization of a Mueller matrix. The DI is defined as $$DI[M] = \frac{\sqrt{\left( \sum_{i,j=0}^{3} M_{i,j}^2 \right) - M_{0,0}^2}}{\sqrt{3}\, M_{0,0}}. \quad (14)$$

The Depolarization Index" is in widespread use to characterize the "strength" or "magnitude" of the depolarization but we will see that this metric can produce misleading results. The DI can vary between zero and one. The DI equals one for non-depolarizing Mueller matrices and equals zero for the ideal depolarizer Mueller matrix, ID $$ID = \begin{bmatrix} 1 & 0 & 0 & 0 \\ 0 & 0 & 0 & 0 \\ 0 & 0 & 0 & 0 \\ 0 & 0 & 0 & 0 \end{bmatrix}. \quad (15)$$

the Mueller matrix which completely depolarizes all incident polarization states so that only unpolarized light exits. The numerator of the Depolarization Index is the Euclidean distance from the ideal depolarizer to the Mueller matrix in a sixteen dimensional space formed from the sixteen elements. The denominator is the radius of the hyperspherical surface of nondepolarizing Mueller matrices for that $M_{00}$. So the DI is the fractional distance of a Mueller matrix along a line segment from ID to the hyperspherical surface for nondepolarizing Mueller matrices. The Depolarization Index is not a consistent metric of the amount of depolarization.

Problems with the Depolarization Index

Any matrix of the form $$CD = \begin{bmatrix} 1 & a & b & c \\ 0 & 0 & 0 & 0 \\ 0 & 0 & 0 & 0 \\ 0 & 0 & 0 & 0 \end{bmatrix}, \sqrt{a^2 + b^2 + c^2} \le 1. \quad (16)$$

is a complete depolarizer and only outputs unpolarized light with DoP=0 for any incident polarization state. But the Depolarization Index for these matrices varies over the range from zero to 0.577, $$DI = \frac{\sqrt{a^2 + b^2 + c^2}}{\sqrt{3} M_{00}}, 0 \le DI \le \frac{1}{\sqrt{3}} \approx 0.577. \quad (17)$$

Therefore the Depolarization Index is not useful for describing the DoP output by Mueller matrices which can only output unpolarized light with DoP=0. DoP may have meaning in a sixteen-dimensional Mueller matrix space, but it has problems in describing the average DoP output by a highly depolarizing process with diattenuation, indicated by the parameters a, b, and c. Thus the present invention describes more useful and understandable metrics for describing depolarization than the Depolarization Index.

With the previous discussion of Mueller matrices as background, we may discuss U.S. Pat. No. 5,822,035 to Bille which describes a Mueller matrix ophthalmic polarimeter and its application to the measurement of corneal retardance. But despite measuring the Mueller matrix of the cornea and the ocular tissue Bille's invention does not describe how to determine the depolarization or diattenuation of ocular tissues or any other samples. Thus, Bille does not analyze determine variations of the depolarization with different incident polarization states of any material, let alone ocular tissue.

An example of retinal Mueller matrix imaging is described in the paper Confocal Scanning Laser Ophthahmoscopy of Mueller-matrix Polarimetry by Bueno and Campbell. They describe an optical system to perform Mueller matrix imaging measurement of the retina and provides an example of a retinal Mueller matrix image. They uses the Mueller matrix image to compare pixels in small regions to calculate the combination of illuminating polarization state and analyzer which provide the best and worst signal to noise ratio. They then apply the best combination to acquire images with improved image quality. But their method does not address how to characterize the depolarization or diattenuation of any material, let alone ocular tissue.

Depolarization of the retina is addressed in the very recent proceedings paper "Depth-Coded polarization imaging" by Elsner, Weber, Cheney, Smithwick, and Burns. They acquired images using the GDx by measuring forty intensities in the cross-polarized channel. These intensities have a roughly sinusoidal variation as a function of the rotating half wave retarder angle. The minimum intensity is taken as the most depolarized state and the intensity recorded pixel by pixel into an image. This measurement and algorithm can measure a mixture of depolarization, retardance, and diattenuation but as will be shown shortly is still several steps removed from a complete depolarization measurement. The method of Elsner et al. provides as close to a complete depolarization measurement as can be obtained with an off-the-shelf GDx. Further analysis of the method of Elsner et al. follows.

In the crossed polarized channel of the GDx the generated and analyzed polarizations are always orthogonal linear polarizations (90° apart). The generated signal comes from a linear polarized beam through a rotating half wave linear retarder producing a linear polarization which rotates at twice the speed of the retarder. The analyzed beam goes back through the same rotating half wave linear retarder then into a polarizer at 90° to the initial polarizer. The analyzed state is a rotating linear state 90° from the generated state.

Any depolarizer which is placed between crossed linear polarizers produces a depolarized (unpolarized) component which cannot be extinguished by the analyzing polarizer. With only the presumed linear retarder (the NFL) in the sample compartment a sinusoidal signal is produced which goes to zero intensity when the retarder is aligned with the polarization generator or polarization analyzer. The method of Elsner et al. exploits the fact that when the retarder also has a depolarization component the signal will not go to zero and the depolarization is sensed. Here, the minimum value in the sinusoidal signal is presumed to be due to depolarization.

One limitation of the method of Elsner et al. is that if the sample has retardance and diattenuation which are not aligned then the signal will not go to zero but the leakage is not due to depolarization. Another limitation of the method of Elsner et al. is that if the sample has elliptical diattenuation the signal will not go to zero and the depolarization measurement may not be accurate. A further limitation of the method of Elsner et al. is that if the sample has circular retardance or elliptical retardance the signal will not go to zero and the depolarization measurement may not be accurate. Thus, with the method of Elsner et al., is not possible to tell what fractions of depolarized light, light coupled by diattenuation, and light coupled by retardance are present in this polarization metric.

The method of Elsner et al. is a fine attempt to get close to the depolarization information in the sample but the ability to measure depolarization accurately is limited by the apparatus and algorithm. The present invention describes an apparatus and algorithm to accurately measure the depolarization, and since depolarization is a complex phenomena, to provide a plurality of metrics describing the samples depolarization.

Therefore what is desired, as discovered by the present inventors, is a polarization imaging method, apparatus, and computer program product which is not limited to measuring linear retardance but can also measure diattenuation and measure all nine degrees of freedom of depolarization. Such a device will be suited to detecting lesions in the retina and other parts of the eye, detecting the characteristics of retinal blood vessels, analyzing the order of the RPE cell packing, and many other imaging tasks. Such a device will also be suited to active imaging of the environment and remote sensing, as well as optical testing of optical systems, as well as other polarimetry operations.

SUMMARY OF INVENTION

The present invention includes a method, apparatus, and computer program product configured to analyze a Mueller matrix, Mueller matrix image, or Mueller matrix spectrum, or any other representation which completely describes the polarization transformations of a sample, to calculate and visualize useful depolarization parameters associated with different forms of depolarization, disorder, and sub-pixel averaging.

In one embodiment, the Mueller matrix algorithms are applied to retinal and other ophthalmic imaging. In another embodiment, the Mueller matrix algorithms are applied to active imaging of the environment and remote sensing. Imaging tasks where the invention may provide image enhancement include separating manmade from natural objects, detecting manmade objects under trees or camouflage cloth, detecting mines and disturbed earth, assessing the state of clouds and turbid media, imaging in smoke, imaging under water and in the sea, and other similar imaging and classification tasks where significant randomness is present in the light matter interactions.

Other embodiments address optical testing of optical systems. Considerable information on the order in liquid crystals, particularly for displays such as computer monitors, projectors, and LCoS TVs is obtained through the application of the invention. Other optical testing embodiments include the identification of bubbles and defects in optical materials and their identification and quantification, assessments of surface roughness, subsurface cracks and other surface defects in optical surfaces, windows, mirrors, silicon wafers, and other surfaces. Other embodiments address industrial testing and process control where a series of samples or manufactured products can be examined and compared on the basis of depolarization characteristics or the combination of depolarization and diattenuation and/or retardance properties. In all of these embodiments, the classification of condition and identification of defects is enhanced because of the large number of depolarization parameters.

The Mueller matrix analysis methods of the present invention are separated into those algorithms and metrics which evaluate (1) only depolarization, (2) those which calculate combinations of depolarization, polarizance and diattenuation, (3) those which evaluate combinations of depolarization and retardance, (4) and those which combine diattenuation, retardance, and depolarization. The Mueller matrix analysis methods of the present invention are also applicable to non-optical polarimetry, such as X-ray polarimetry, UV/IR polarimetry, and polarimetry of other spectra.

BRIEF DESCRIPTION OF THE DRAWINGS

A more complete appreciation of the present invention and many of the attendant advantages thereof will be readily obtained as the same becomes better understood by reference to the following detailed descriptions and accompanying drawings.

DETAILED DESCRIPTION OF THE INVENTION

Figure 1:
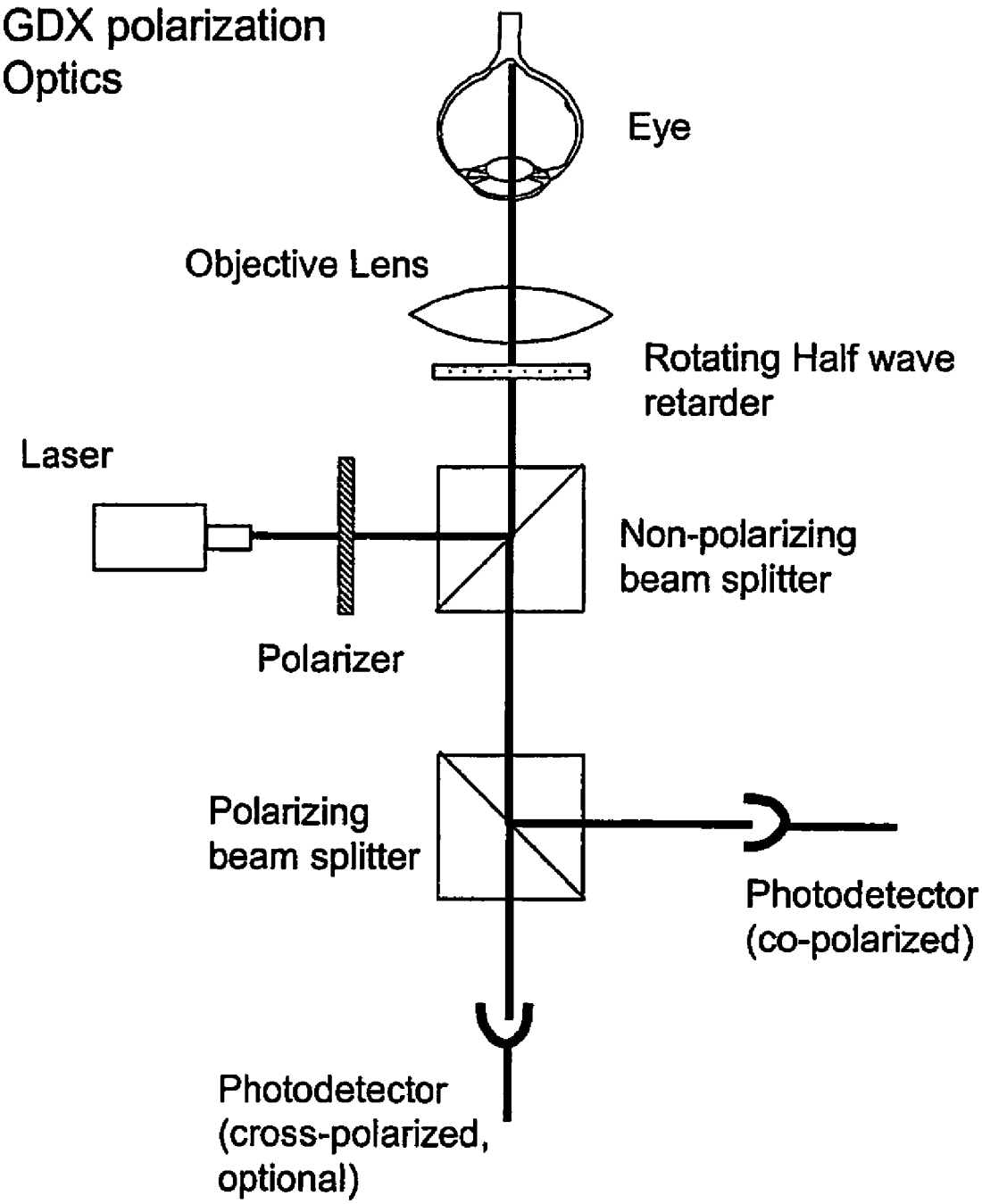
FIG. 1 is a simplified block diagram of a conventional retinal polarimeter.

One cannot determine from a simple examination of a Mueller matrix how much depolarization the corresponding light/matter interaction causes because the change in the degree of polarization is a function of the incident polarization state. For most depolarizing light/matter interaction, some incident polarization states are depolarized more, and other states less. The invention provides new and useful ways of analyzing the variations of depolarization will reveal important characteristics of a sample.

Conventional systems and techniques are characterized by deficiencies of the Depolarization Index relative to describing the magnitude of depolarization. Here, a new depolarization metric is introduced as a single number which varies from zero to one to summarize the magnitude of depolarization of the light exiting a sample. This new metric is the Average Degree of Polarization or AverageDoP. The Average Degree of Polarization is calculated by integrating the DoP as the incident state, S, varies over the entire Poincaré sphere and normalizing with $1/4\pi$ for the area of the sphere, $$AverageDoP = \frac{\int_0^\pi \int_{-\pi/2}^{\pi/2} DoP(M \cdot S(\theta, \phi)) \mathrm{Cos}(\phi) d\theta d\varphi}{4\pi}. \quad (18)$$

The terms $\mathrm{Cos}(\phi)$ $d\theta d\phi$ integrate the incident polarization state over the Poincaré sphere. The AverageDoP varies from zero to one. When AverageDoP is equal to one the exiting light is always completely polarized indicating that no depolarization has occurred. A value near one indicates little depolarization. When AverageDoP equals zero the exiting light is always completely depolarized irregardless of the incident polarization state; only unpolarized light exits the interaction. Contrast this result with the Depolarization Index which varies from zero to 0.577. In practice the AverageDoP is most readily calculated using standard numerical integration routines.

The Average Degree of Polarization and its application to various polarization measurements, polarization images, and polarization spectra is the first part of the present invention.

The second part is another metric for the magnitude of depolarization which varies from zero to one which is obtained by weighting the AverageDoP calculation by the exiting flux yielding a measure, the WeightedDoP, defined as $$WeightedDoP = \quad (19)$$

$$\frac{\int_0^\pi \int_{-\pi/2}^{\pi/2} (M(0) \cdot S(\theta, \phi)) DoP(M \cdot S(\theta, \phi)) \cos(\phi) d\theta d\varphi}{\int_0^\pi \int_{-\pi/2}^{\pi/2} (M(0) \cdot S(\theta, \phi)) \cos(\phi) d\theta d\varphi}.$$

$M(0)$ indicates the top row of the Mueller matrix; the dot product of $M(0)$ with the incident polarization state yields the exiting flux. The numerator weights the exiting DoP by the exiting flux while the denominator calculates the average exiting flux. So the WeightedDoP weights the DoP of bright exiting states more than dim exiting states. This averaging the DoP over the intensity exiting light versus the AverageDoP which weights all input states equally. For a depolarizing Mueller matrix constructed from a sum of retarder Mueller matrices, the transmission is the same for all incident polarization states so the WeightedDoP equals the AverageDoP. But for Mueller matrices involving polarizers, the transmission varies considerably with the incident polarization state and significant differences between these two metrics occur. WeightedDoP can be usefully applied for example to beams exiting polarizers with some depolarization where some incident states generate little exiting light and those dim exiting states are to be weighted less.

The next two parts of the invention are two metrics describing the variation of depolarization properties with incident polarization state, DoP surfaces and DoP maps. The DoP surface for a Mueller matrix, M, is formed by moving normalized Stokes vectors, S, on the surface of the Poincaré sphere radially inward to a distance $DoP(S'=M\cdot S)$ from the origin, plotted for all incident S on the surface of the Poincaré sphere. The DoP surface results from the product of a scalar, the DoP, and a vector, $(S_1, S_2, S_3)$, formed from the last three elements of the normalized incident Stokes vector, $$DoPSurface(M, S) = \quad (20)$$

$$\frac{\sqrt{S_1'(M, S)^2 + S_2'(M, S)^2 + S_3'(M, S)^2}}{S_0'(M, S)}(S_1, S_2, S_3),$$

for all $(S_1^2 + S_2^2 + S_3^2)^{1/2} = 1$.

The DoP map for a Mueller matrix is a contour plot, surface plot, false color plot, etc, of the DoP of exiting light as a function of the incident polarized state and represents a "flattened" DoP surface. Here DoP map is plotted with axes θ(polarization ellipse major axis orientation) and Degree of Circular Polarization, DoCP. Those skilled in the art of polarization mathematics realize that this is only one of many projections of the sphere and that the choice of a particular projection is arbitrary. Mapping the DoP over any projection of the sphere onto a plane provides the same information on DoP variations. Similarly there is flexibility in the choice of parameterization of the polarized Stokes vectors. In general the DoP map provides a more quantitative visualization of maxima, minima, saddles, and other features of the depolarization variation than the DoP surface. An example is provided in a later section of this document.

These DoP surfaces and DoP maps are detailed metrics which completely characterize depolarization. Those skilled in the mathematics of polarization calculus will realize that the incident Stokes vectors can be parameterized in different ways leading to a stretching or distortion of these surfaces and maps without changing the underlying information. For example the maxima and minima are unchanged by such a parameterization change.

Similarly these surfaces and maps are defined for the incident state but can also be defined with minor modifications in terms of the corresponding exiting polarization state on the Poincaré sphere by the modified equation $$OutputDoPSurface(M, S) = \quad (21)$$

$$\frac{\sqrt{S_1'(M, S)^2 + S_2'(M, S)^2 + S_3'(M, S)^2}}{S_0'(M, S)} \frac{(S_1', S_2', S_3')}{\sqrt{S_1'^2 + S_2'^2 + S_3'^2}},$$

for all S. The normalization with the square root in the denominator is necessary since the output Stokes vector is in general depolarized. This surface and corresponding map associated the exiting DoP with the location of the exiting Stokes vector on the Poincaré sphere.

Several very important depolarization metrics which constitute a part of this invention may be defined in terms of the DoP surface:

Maximum DoP,
Maximum S, or Stokes vector with the least depolarization,
Minimum DoP,
Minimum S, or Stokes vector with the most depolarization,
Maximum DoP—Minimum DoP.

The Maximum DoP is the largest value found in the DoP map. Associated with the Maximum DoP is a very important depolarization parameter, Maximum S, the incident polarization state with the least depolarization. Maximum S is applicable for example to using Liquid Crystal devices and retarding films in Liquid Crystal displays. Depolarization in such optical elements leads to light which cannot be blocked by the analyzing polarizer, the element which modulates the intensity. The depolarized light can only be half blocked by the analyzer and thus limits the darkness of the dark or black state of the display. Thus it is important that the Maximum S is near the operating polarization state of the element to ensure high contrast, especially for the dark end of the operating range of the display.

The Minimum DoP is the minimum value on the DoP map and the Minimum S is the state which is most depolarized. Maximum DoP and Minimum DoP can be calculated by applying standard maxima finding algorithms to the DoP function or by sampling the DoP for a large number of polarized Stokes vectors and taking the largest DoP in the list.

Two other metrics which constitute part of this invention are the difference, MaximumDoP−Minimum DoP and the angle between Maximum S and Minimum S on the Poincaré sphere.

Metrics Which Combine the Depolarization and Diattenuation

The incident Stokes vector, $S_{max}$, is the state for which a series of polarization elements used for a measurement, called a polarizer analyzes, has its maximum transmittance. The degree of polarization for the analyzed state $DoP(S_{max})$ is an important parameter for a polarizer. Similarly polarizers are used to extinguish the state $S_{min}$, so the depolarization metric $DoP(S_{min})$ contains important information on the nature of the light which leaked though at the intended extinction point. If $DoP(S_{min})$ is close to one the polarizer can be improved by adding a second polarizer in sequence. If DOP $(S_{min})$ is low little can be done to further improve the polarizer extinction. The $DoP(S_{max})$ and $DOP(S_{min})$ are two depolarization metrics which are part of the invention.

Metrics Which Combine the Depolarization, Diattenuation and Polarizance to Reveal Order Dependence It is frequently possible to determine in a sample comprised of a series of polarization interactions whether depolarization is occurring toward the front of the sample or closer to the exit. For example, consider a polarizer which gets contaminated with dirty oil on one side and the oil introduces some depolarization into the element. By applying the next part of the present invention, it is often possible to identify if the depolarizing oil is on the front or back surface.

For many polarization elements, the diattenuation and polarizance have the same magnitude and their vectors have axes aligned on the Poincaré sphere. But for inhomogeneous polarization elements, combinations of diattenuators and retarders with different axes, the polarizance axis is different from the diattenuation axis. For these inhomogeneous polarization elements in the absence of depolarization, the magnitudes of the diattenuation and polarizance remain equal, only the locations of the diattenuation and polarizance axes on the Poincaré sphere change.

Depolarization introduces an important and measurable change the diattenuation and polarizance by indicating if the depolarization tends to act toward the beginning of a series of polarization interactions or toward the end. Consider three combinations of a horizontal linear polarizer and an ideal depolarizer. Example Mueller matrices are (1) DD1, a horizontal polarizer followed by an ideal depolarizer, and (2) DD2, an ideal depolarizer followed by a horizontal polarizer. For comparison a parallel configuration, DD3, with an ideal depolarizer filling one half an aperture and a horizontal polarizer filling the other half is compared.

$$DD1 = \begin{pmatrix} 1 & 0 & 0 & 0 \\ 1 & 0 & 0 & 0 \\ 0 & 0 & 0 & 0 \\ 0 & 0 & 0 & 0 \end{pmatrix}, \quad (22)$$

$$DD2 = \begin{pmatrix} 1 & 1 & 0 & 0 \\ 0 & 0 & 0 & 0 \\ 0 & 0 & 0 & 0 \\ 0 & 0 & 0 & 0 \end{pmatrix}. \quad (23)$$

$$DD3 = \frac{1}{2}\begin{pmatrix} 2 & 1 & 0 & 0 \\ 1 & 1 & 0 & 0 \\ 0 & 0 & 0 & 0 \\ 0 & 0 & 0 & 0 \end{pmatrix}. \quad (24)$$

Comparing the first row and first column it is seen that when a depolarizer precedes a polarizer or diattenuator, as with matrix DD1, the diattenuation is smaller than the polarizance. When a depolarizer is followed by a polarizer or diattenuator, as with matrix DD2, the polarizance is smaller than the diattenuation. In example, DD3, where the diattenuators and depolarizer act in parallel, by sharing an aperture side-by-side the diattenuation and polarizance are equal. Thus part of the present invention is the application of a depolarization metric formed from the diattenuation to polarizance ratio, called the DPRatio, $$DPRatio = \frac{Diattenuation}{Polarizance} \quad (25)$$

$$= \frac{\sqrt{\sum_{i=1}^{3} M_{0,i}^2}}{\sqrt{\sum_{j=1}^{3} M_{j,0}^2}}$$

-continued $$= \frac{\sqrt{M_{0,1}^2 + M_{0,2}^2 + M_{0,3}^2}}{\sqrt{M_{1,0}^2 + M_{2,0}^2 + M_{3,0}^2}}$$

A DPRatio less than one indicates that depolarization is tending to occur toward the front of the interaction. A DPRatio greater than one indicates depolarization is tending to occur toward the end of the interaction. A DPRatio very close to one indicates no preference or measurable order dependence. Those skilled in the art realize that the logarithm of this DPRatio and other similar mathematical forms convey the same information from the Mueller matrix on order dependence of diattenuation, polarizance and depolarization.

Metrics Which Analyze the Depolarization and Retarder Order Dependence

Similarly for a Mueller matrix which is dominated by retardance and depolarization, where the diattenuation and polarizance are near zero, a metric is defined as part of the present invention which evaluates the order dependence of retardance and depolarization. This metric for the order dependence of retardance and depolarization, RetDep, is defined as $$RetDep = \frac{AvMagRows}{AvMagCol} = \frac{\sum_{j=1}^{3}\sqrt{\sum_{i=1}^{3} M_{i,j}^2}}{\sum_{i=1}^{3}\sqrt{\sum_{j=1}^{3} M_{i,j}^2}}. \quad (26)$$

Since retardance properties are found in the lower right 3×3 sub-matrix, this equation evaluates the average magnitude of the rows compared to the average magnitude of the columns in this sub-matrix. This parameter is greater than one when the retardance tends to occur first, before the depolarization, and is less than one when the depolarization tends to occur before the retardance. This metric, RetDep, has special application to liquid crystal devices which are predominantly retarders but frequently suffer from depolarization problems.

Metrics Which Combine the Depolarization, Diattenuation, Polarizance and Depolarization and Reveal Order Dependence The present invention contains a metric for Mueller matrices, RowsColumns, which contain all of the polarization properties and identifies the order dependence tendency of the depolarization. The metric RowsColumns $$RowsColumns = \frac{\sum_{j=0}^{3}\sqrt{\sum_{i=0}^{3} M_{i,j}^2}}{\sum_{i=0}^{3}\sqrt{\sum_{j=0}^{3} M_{i,j}^2}} \quad (27)$$

is similar to RetDep except the summation indices start at zero rather than one. The magnitudes of entire rows and columns, not the submatrix, are evaluated for their average. In applying this metric to Mueller matrix images the results are commonly very close to 1.0, often within 0.0001, but still provide a consistent indication of order dependence.

Figure 2:
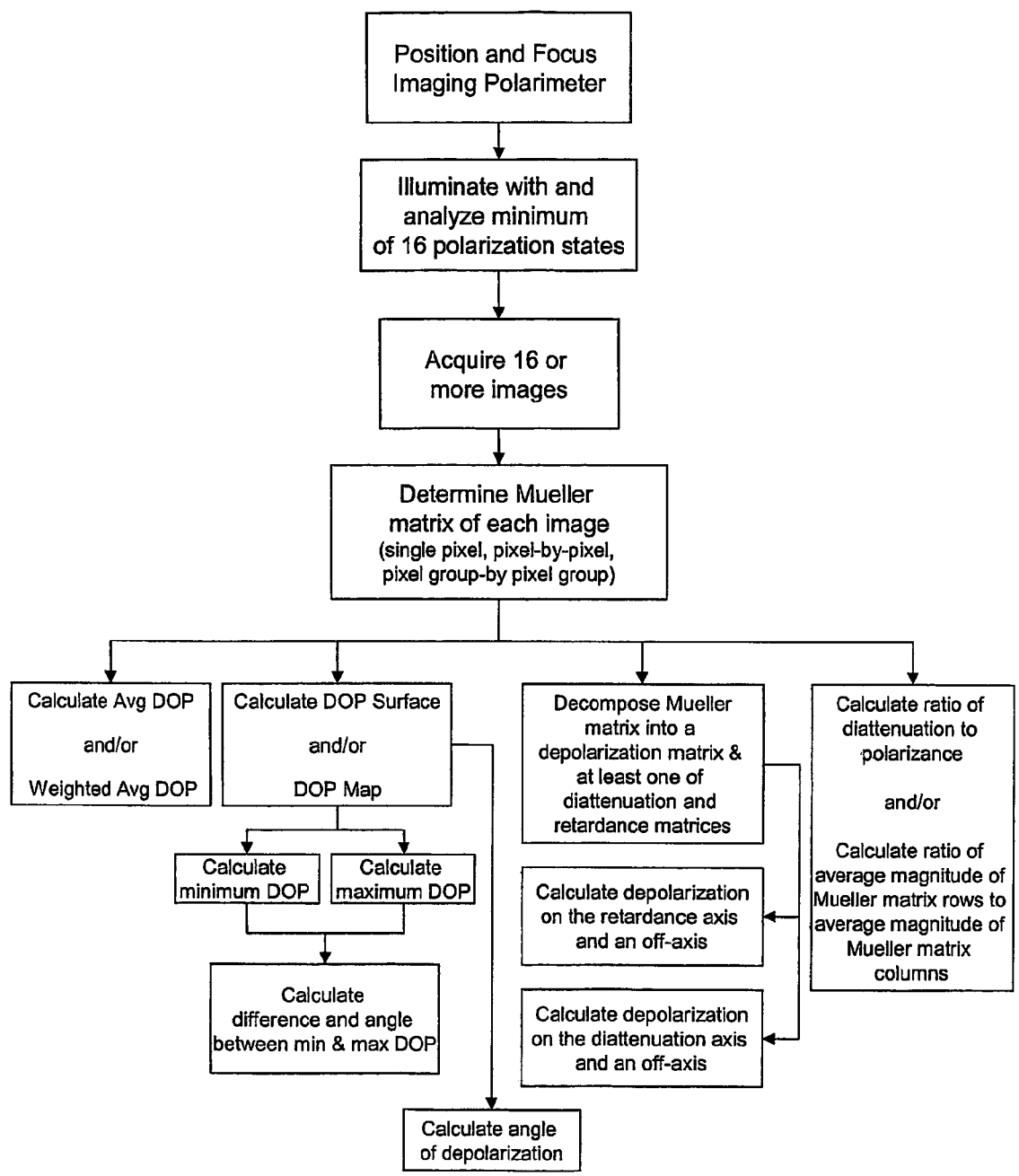
FIG. 2 is a flow chart representation of at least one embodiment of the present invention.

The preceding method steps are summarized in FIG. 2. The method begins with positioning and focusing an imaging polarimeter. An object is then illuminated with a series of at least 16 polarization states. Each of these states are analyzed and 16 or more images are obtained. These images are stored in a computer for further analysis. A Mueller matrix is obtained for each image. The matrix may be obtained by analyzing a single pixel, analyzing the image on a pixel-by-pixel basis, or by analyzing the image on a pixel group-by-pixel group basis. The image may be cropped or otherwise adjusted to an area of interest. Once the Mueller matrix is obtained, features are identified by one of a set of optional computations. The average degree of polarization and/or the weighted average degree of polarization may be calculated. From one or both of these values, features may be identified.

Alternatively, the degree of polarization surface and/or degree of polarization map may be calculated. From the degree of polarization surface and/or degree of polarization map, minimum and/or maximum degrees of polarization may be calculated. If both the maximum and minimum degree of polarization is calculated, then the difference between these values may also be calculated. Also from the degree of polarization surface and/or degree of polarization map, one may optionally calculated the degree of polarization. From one or more of these values, features may be identified.

Alternatively, the Mueller matrix may be decomposed into a depolarization matrix and at least one of a diattenuation matrix and a retardance matrix. From these matrices, one may calculate the depolarization relative to the corresponding diattentuation or retardance axis. Also, one may calculate the depolarization relative to the corresponding diattentuation or retardance off-axis (typically 45°). From one or more of these values, features may be identified.

Alternatively, the Mueller matrices are used to calculate the ratio of diattenuation to polarizance. Alternatively, the Mueller matrices are used to calculate the ratio of the average magnitude of Mueller matrix rows to the average magnitude of Mueller matrix columns. From one or more of these values, features may be identified.

Figure 3:
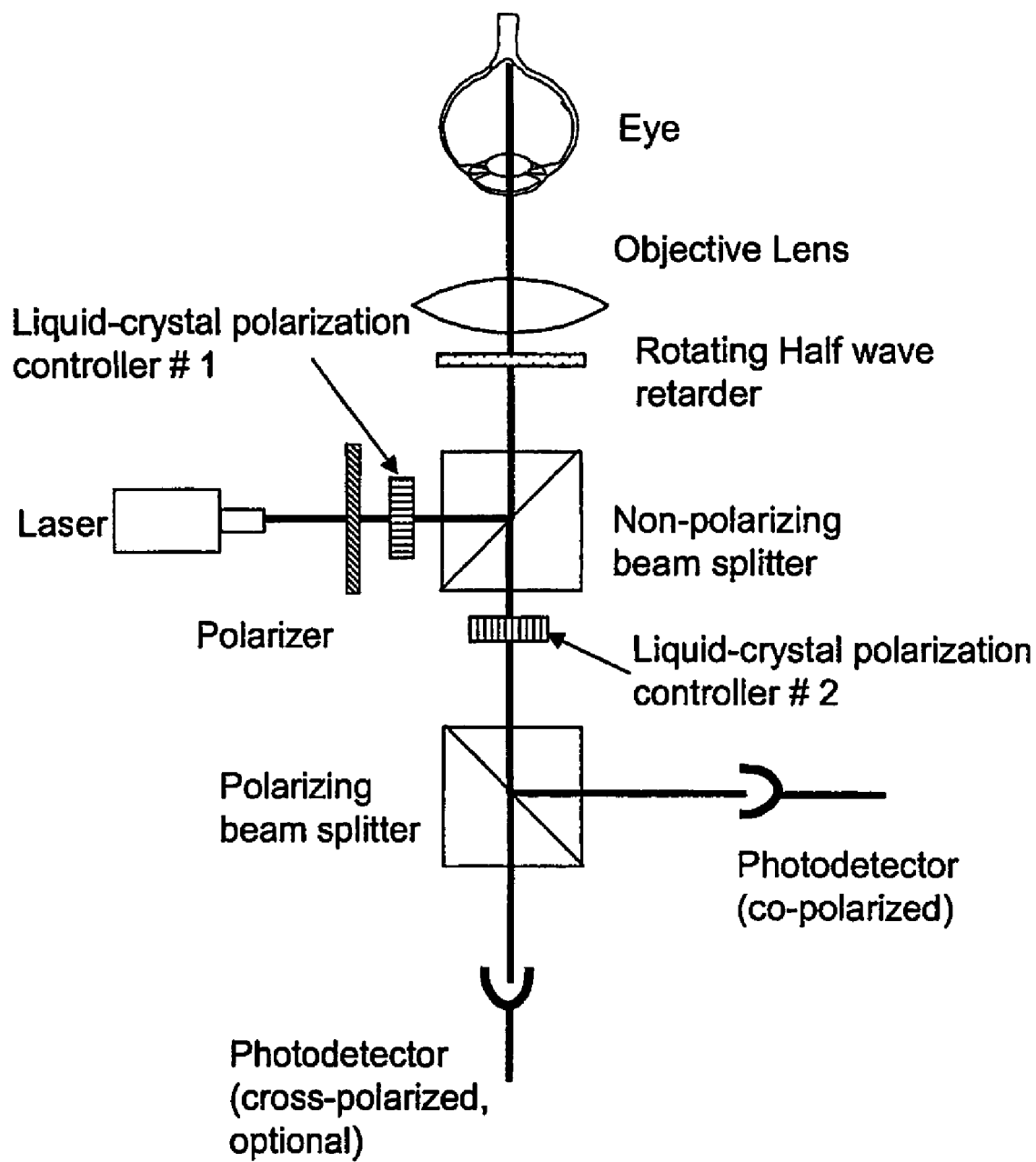
FIG. 3 is a block diagram of a retinal polarimeter modified to execute at least one of the steps shown in FIG. 2.
Figure 4:
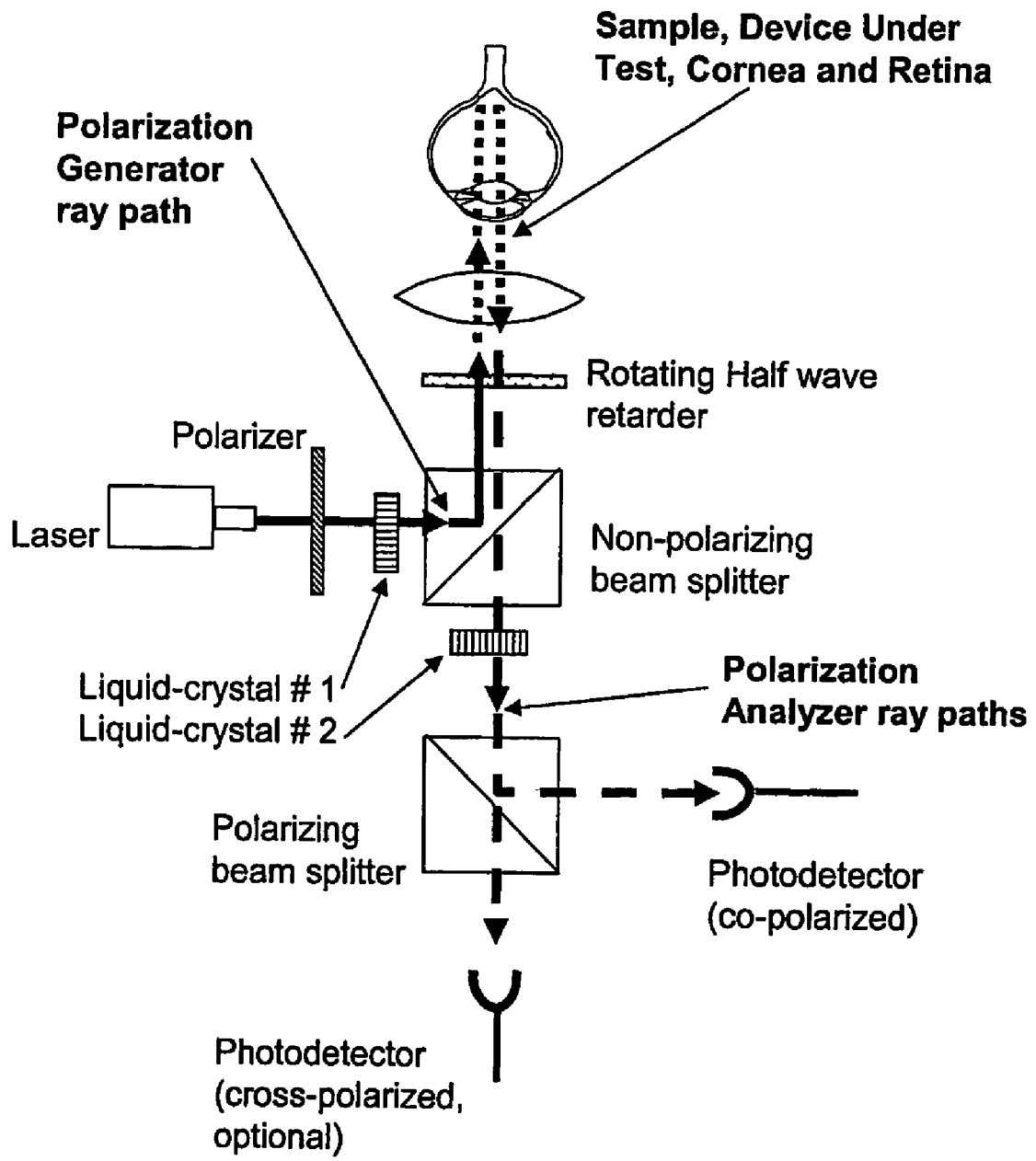
FIG. 4 is a block diagram showing the optical path of the embodiment shown in FIG. 3.

FIGS. 3 and 4 are block diagrams of one embodiment of the present invention, in which a conventional GDx device shown in FIG. 1 is modified to obtain the data used in the calculations shown in FIG. 2. As previously noted, the current GDx cannot measure depolarization because it does not measure the full Mueller matrix of a sample (e.g., an eye). In the present embodiment, two liquid crystal polarization controllers are placed in the path of the laser beam. The liquid crystal polarization controllers have their axes oriented 45° to the axis of the polarizing beam splitter. These liquid crystal polarization controllers are electrically adjustable linear retarders capable of changing retardance over more than one wave of retardation. The first liquid crystal polarization controller is inserted in the polarization generator light path after the polarizer and before the nonpolarizing beam splitter. Without the first liquid crystal polarization, only linear polarization states are generated. With the first liquid crystal polarization, linear, elliptical and circular polarization states are generated. Without the second liquid crystal only analyze linear polarization states can be analyzed. With the second liquid crystal inserted just before the polarizing beam splitter, linear, elliptical and circular polarization states may be analyzed.

In this embodiment, four sets of GDx images are acquired in rapid succession. For the first set of images the two liquid crystals are adjusted to +7/8 and +7/8 waves retardance. For the second set of images the two liquid crystals are adjusted to +7/8 and +9/8 waves retardance, for the third to +9/8 and +9/8 waves, and for the fourth set to +9/8 and +7/8 waves. From this enlarged data set the Mueller matrix image is calculated by the methods described in the Polarimetry, Chapter 22 of the Optical Society Handbook of Optics volume 2 by Chipman. Accurate measurement requires that all the generated and analyzed polarization states are carefully calibrated before operation. The algorithms and methods of the present invention then operate upon the Mueller matrix image to render images of the depolarization metrics.

Those skilled in the art of polarimetry understand that the sets of retardance settings for the two liquid crystals are arbitrary and can assume a large set of values and that four is not the only number of sets of modified GDx images which can measure the data for the Mueller matrix calculation, as is evident from a reading of the Polarimetry chapter. Further many combinations of retardances are used in our system to obtain the Mueller matrix by similar by different pairs of generated and analyzed states.

Optical Configurations for Ocular and Retinal Imaging

Retinal imaging polarimeters, retinal spectropolarimeters, and polarimeters for other parts of the eye and can be constructed in a variety of optical illumination configurations and imaging configurations depending on the measurement objectives. Four basic configurations for illuminating the eye and collecting the reflected light are disclosed below.

The first configuration includes the use of a imaging polarimeter where a portion of the eye is illuminated through the cornea and the light from the target ocular tissue is collected through the cornea. The depolarization evaluation methods disclosed above are applied to the measured polarization data. This method of transcorneal illumination and collection is the most common configuration for optical diagnostics within the eye because illuminating and collecting light through the cornea is relatively non-invasive. This is the configuration of the GDx retinal polarimeter and of OCT retinal imagers.

This method of transcorneal illumination and collection of light from the eye has certain drawbacks which are addressed below. Among these drawbacks are back reflections or glints from the cornea, crystalline lens, and particularly for our purposes from the centers of retinal blood vessels. These back reflections make the quantitative measurements necessary for precision polarimetry difficult and often impossible to apply to retinal blood vessels.

The second configuration includes an ophthalmic polarization measurement where the illumination of ocular tissue is performed when the light from a polarization state generator emerges from an optical probe placed inside the eye. A fraction of the light scattered out of the eye through the cornea is collected and measured by the polarization state analyzer. An intravitreal fiber optic probe can be used to back illuminate the iris, the lens, or cornea of the eye. The probe can be a GRIN lens, endoscope, or small optical relay system or the light source itself can be placed into the eye along with the necessary polarization elements. Or, in a preferred embodiment of this invention, an illuminating probe is placed into the vitreous chamber to illuminate the retina and the scattered light which passes through the lens and iris is collected and relayed into the polarization state analyzer for measurement. This measurement may be a retardance measurement or a measurement of diattenuation, depolarization, or any combination of these three properties. Since the illuminator, such as fiber optic or GRIN lens, is placed into the vitreous chamber, it illuminates the retina and the blood vessel from the side. This side illumination illuminates behind the vessels which are typically 300 microns or more above the retinal pigment epithelium (RPE). Some of this light scattered from the RPE single passes through the artery or vein and after exiting the eye through the cornea is collected by an imaging system and the flux is measured. The drawback of this part of the present invention is that placing an illuminating probe into the vitreous or other part of the eye an invasive surgical procedure. The great advantage of the intraocular illumination is that it measures valuable information which is not available by transcorneal illumination. Further inserting an illuminator into the vitreous is a common procedure in retinal surgery. Intraocular illumination greatly reduces glints. Intraocular illumination allows blood vessels to be measured by polarimetry in single pass. Other tissues are probed and measured with different light paths than occur with transcorneal illumination providing different information. The measurement of a Mueller matrix image or spectra, retardance, diattenuation, and depolarization parameters by intraocular illumination is accomplished as discussed previously.

The third optical configuration encompasses the illumination of ocular tissue through the cornea, where light for the polarization analyzer is collected by a probe placed into the eye. This configuration allows side-scattered rather than backscattered component to be collected. By placing the probe close to the tissue of interest, a higher resolution image or an image formed from a larger solid angle of reflected light is obtained. The measurement of a Mueller matrix image or spectra, retardance, diattenuation, and depolarization parameters by intraocular light collection is accomplished as discussed previously.

The fourth configuration for ocular polarimetry includes the illumination of ocular tissue by a probe placed into the eye, where the light for the polarization analyzer is collected by a probe placed into the eye. This method combines the advantages of the second and third configurations into one polarimetric measurement with great flexibility on the directions of incident and collected light and best control of the stray light which naturally occurs within the vitreous and other cavities of the eye. The measurement of a Mueller matrix image or spectra, retardance, diattenuation, and depolarization parameters by intraocular illumination and intraocular light collection is accomplished as discussed previously.

The methods for ocular and retinal imaging described above are summarized in FIG. 5. The methods begin with a modulation of polarization in a polarization state generator. The retina is then illuminated either through the cornea or via a probe inserted into the eye. The light interacts with the ocular tissue producing retardance, diattenuation, and depolarization parameters. The light reflected off the retina is either collected by a receiver located outside of the eye or inside of the eye. The collected light is analyzed as discussed previously (i.e., via a polarization state analyzer, the acquisition of at least 16 images, the calculation of a Mueller matrix image, and Mueller matrix analysis as discussed relative to FIG. 2.)

Figure 5:
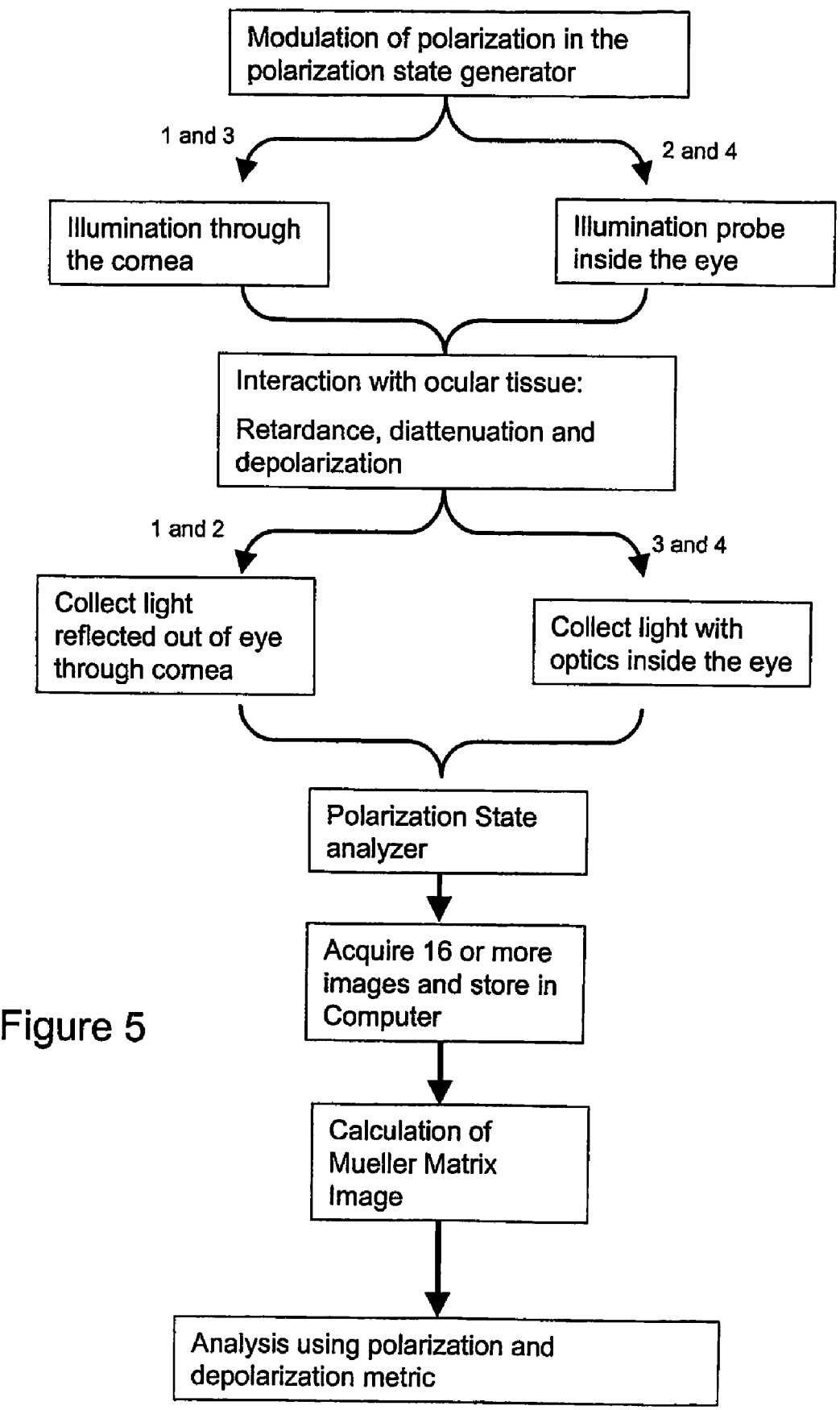
FIG. 5 is a flow chart representation of various embodiments of the present invention.
Figure 6:
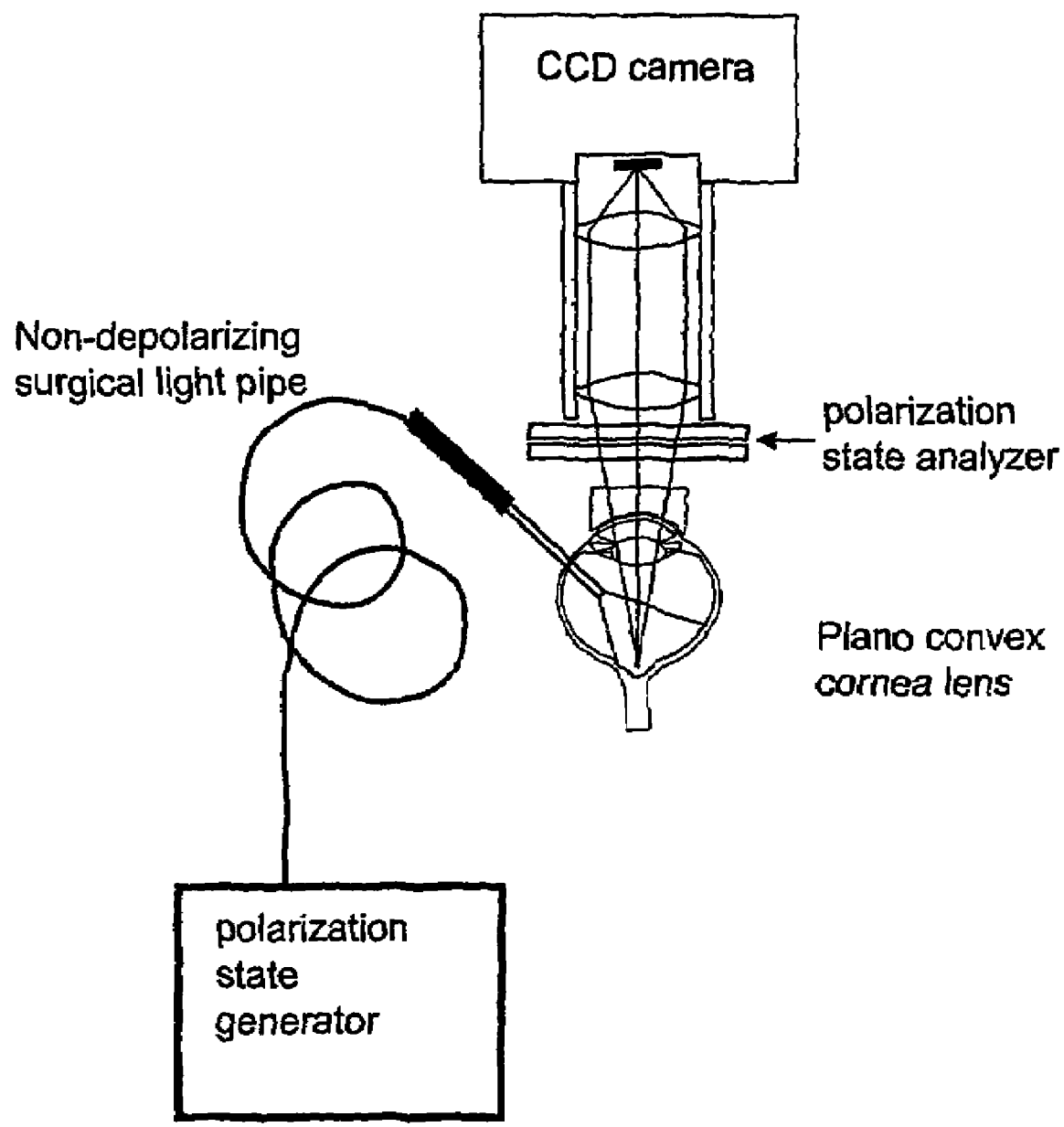
FIG. 6 is a block diagram corresponding to at least one of the embodiments shown in FIG. 5.

FIG. 6 is a block diagram corresponding to some of the embodiments described relative to FIG. 5. One embodiment of the present invention includes a non-depolarizing surgical light pipe configured to pierce the eye and illuminate the retina as described relative to FIGS. 3 and 4. The light pipe is fed by a polarization state generator. Light reflected from the eye is passed through the cornea through a polarization state analyzer to a camera.

Figure 7:
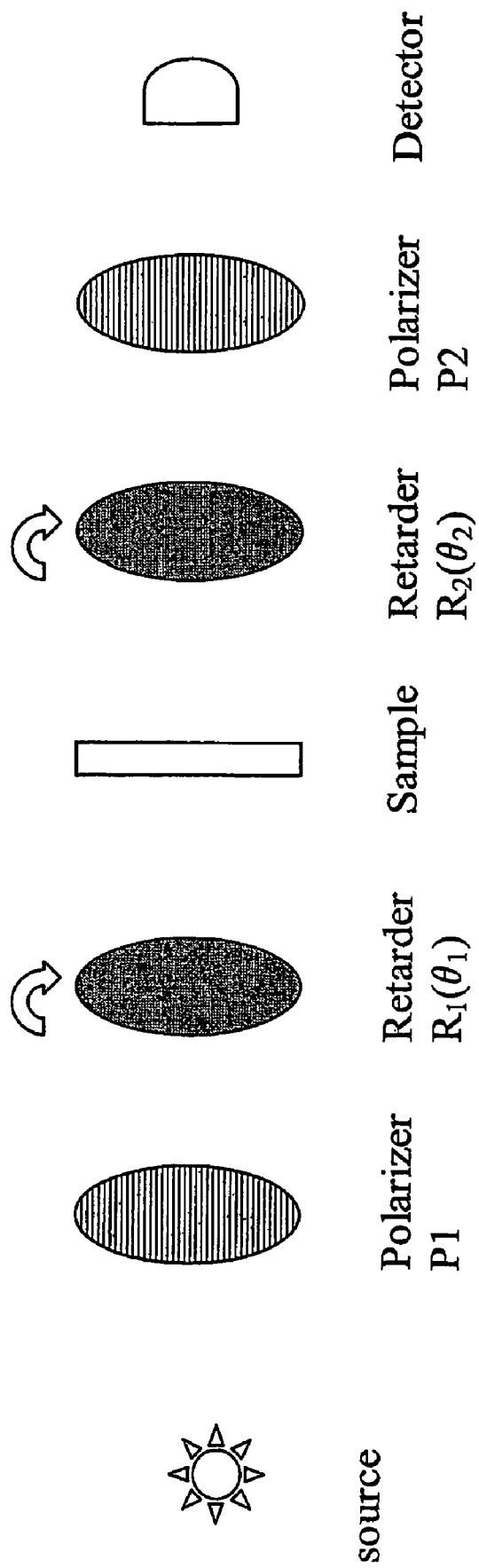
FIG. 7 is a block diagram of a rotating retarder polarimeter used in at least embodiment of the present invention.

FIG. 7 is a simplified block diagram of a rotating retarding polarimeter used in at least one embodiment of the present invention. This device is based on a Mueller matrix imaging polarimeter constructed at the University of Arizona. With this device, a beam from a light source, typically a laser or beam from a monochromator, passes through a polarization generator constructed from a linear polarizer followed by a linear retarder. Light from the generator illuminates the sample and has its polarization modified by the sample. The desired beam from the sample may be the transmitted, reflected, scattered, or diffracted beam. The polarization analyzer is positioned to collect the desired beam. This light passes through the polarization analyzer, a linear retarder followed by a linear polarizer. A lens focuses the beam onto a CCD detector. To perform a measurement the two retarder are rotated to a series of more than 16 positions and an image is acquired by the CCD at each position and transferred to a data storage medium such as a computer hard disk. The data is then reduced pixel-by-pixel to calculate the Mueller matrix resulting in a Mueller matrix image. Algorithms to perform this Mueller matrix measurement and data reduction are contained in Polarimetry, Chapter 22 of the Optical Society Handbook of Optics volume 2 by Chipman. Most commonly, retarder one is moved by a small angle such as 4° between measurements and retarder two is moved by five times the angle, such as 20°, until the first retarder has rotated through 180°. From this Mueller matrix image the depolarization metrics are evaluated to render the various depolarization images of the sample.

In summary, the methods of collecting and manipulating Mueller matrices disclosed above can be applied to the active polarization imaging of biological tissues, for example in the eye. Many tissues have significant polarization characteristics such as the retardance associated with the nerve fiber layer or cornea which arise form the overall structure and order of the cells. In disease states or other conditions the order of these structures can become disrupted or randomized. Thus by measuring and analyzing the degree of polarization for different linear and elliptical polarization states and organizing this information into pixel-by-pixel representations or images of different metrics for the depolarization, these images of the depolarization can assist in the detection and visualization of difficult to detect structures.

For example the depolarization characteristics of an area of the nerve fiber layer may be abnormal and images of the different depolarization metrics may indicate structures difficult to detect in intensity or retardance images. Similarly the retinal pigment epithelium is a well organized layer of hexagonal cells. As a result of age related macular degeneration, the RPE becomes bumpy and bunched and the RPE cells become disordered. Although individual RPE cells cannot be resolved in fundus imaging and retinal polarization imaging, analysis of the degree of polarization of a set of different incident polarization states conveys information on the order of the scattering medium.

Another example concerns the growth of new blood vessels from the choroid through the retinal pigment epithelium and into the retina, or neovascularization, causes disruptions in the photoreceptor layer. These disruptions in the order of the photoreceptor layer can alter the patterns of depolarization. These retinal depolarization signatures can often be further enhanced by placing the illuminating light source into the eye for example into the vitreous, and illuminating from the side. Similarly by collecting the scattered polarized light with optics placed into the eye, different and useful information is obtained than by measurements which illuminate and collect through the cornea, particularly because the photoreceptors are only seen along their axes by transcorneal imaging.

Thus depolarization imaging can assist in the detection and assessment of retinal tissue lesions, neovascularization, edema, drusen, basal deposits, basil laminar deposits by inducing these structures to be visualized in the images created using the methods of the invention.

The reduction of degree of polarization is associated with multiple scattering. Analysis of the variations of depolarization convey information on the dominant orientations of the multiple scattering and can assist imaging into the deeper layers of scattering media Thus analysis of the patterns of depolarization can aid in seeing deeper structures in the retina, the RPE and the choroids As noted previously, the Mueller matrix analysis techniques disclosed above may also be applied to the analysis of surfaces. In analyzing a surface such as a piece of metal, a polarization image of the piece of metal may appear uniform. But below the resolution of the polarimeter the metal surface may have small closely spaced machining marks in the form of small ridges which may be straight or curved. When illuminated with polarized light the variations of the slopes of the metal surface cause a spatial modulation in the polarization state of the specularly and diffusely scattered light. When these spatial variations of polarization state occur below the spatial resolution of the imaging polarimeter they cause a reduction in the degree of polarization of the light. The present invention describes a method for illuminating the sample with a multitude of incident polarization states and by analyzing the different degrees of polarization in the collected light to determine information on the magnitude, orientation, and order of such features below the spatial resolution of the imaging polarimeter. For example, the equivalent polarization element to a typical nearly smooth metal surface, such as machined aluminum or steel, is a linear retarder together with a weak polarizer (diattenuators). The machining marks left in the metal introduce subpixel variations in the retardance and diattenuation of the metal surface when the machining marks are too small to be seen or resolved by the imaging system. By illuminating the metal with linearly polarized states parallel to the grooves, perpendicular to the grooves, at 45° to the grooves, and with various elliptical and circular polarization states and carefully analyzing the degree of polarization of the different beams collected by the imaging polarimeter and analyzing and comparing these degree of polarization patterns with the other polarization properties of the metal surface by the methods of the invention, information is obtained on the magnitude and orientation of the retardance and diattenuation variations of the surface, and indirectly on the residual machining marks. Thus a smooth surface will differ from a surface with significant machining marks in the degree of polarization of the reflected light. A machined surface with parallel straight marks will depolarize a set of incident polarization states differently from a surface with curved marks or random marks. Thus, although the machining marks are not seen or resolved by the imaging polarimeter, although the positions of the marks within the pixels cannot be known from the data, the presence of the polarization variations and their orientation and order can be inferred from the data and the surface classified on the basis of their form, magnitude, orientation, and randomness. The form of these variations can be either subpixel variations in the retardance of the surface or subpixel variations in the diattenuation of the surface.

One application of the invention is the classification of surfaces by the depolarization of their reflected or scattered light. Another application is the industrial inspection of materials and products by analyzing the depolarization of light reflected, transmitted or scattered from these objects. Another application is the analysis of natural scenes by actively illuminated imaging polarimetry to enhance the ability to recognize and distinguish objects in the scene. Examples include imaging tasks such as the detection of mines, buildings and vehicles, finding vehicles and man-made objects under tree canopy or camouflage, and similar tasks.

Also as noted previously, the Mueller matrix analysis techniques disclosed above may also be applied to the analysis of liquid crystals. The liquid crystal devices used in computer monitors, projectors, watch and cell phone displays, and other applications operate as electrically addressable retarders. For optimal operation the polarization characteristics should remain constant within a pixel. Otherwise local polarization state variations result which reduce the degree of polarization of the light. This depolarization limits the ability of the device to render a good black state and reduces the contrast ratio of the liquid crystal device, one of the most important specifications. Conventionally, this depolarization is only tested at the incident polarization state used in the system. By the methods of the invention, by measuring the depolarization for a plurality of polarization states useful information is obtained on the type of variations of polarization properties within a pixel. For example variations in the thickness of a cell are clearly distinguished from variations in the orientation of the liquid crystal molecules because these variations affect the Mueller matrix differently. Since nine depolarization degrees of freedom can be measured, many different types of defects can be associated with different depolarization metrics.

Also, software supporting such calculations would also be applicable to non-optical polarimetry, such as X-ray polarimetery, V/IR polarimetry, and polarimetry of other spectra.

FIG. 7 is a block diagram the overarching system architecture of the present invention. The data discovery system 71 accesses one or more archives of electronically stored material 72 via an interconnection media 70. The databases 72 may be of any commercial or proprietary structure (e.g., SQL, HTML, flat files, object-oriented) and content (e.g., documents, e-mail, annotated images, annotated audio/video, etc.). The data discovery engine 74 performs a filtering and selection operation with compliance word and privilege word criteria which is either pre-stored in a criteria archive 75. The results of the data discovery process are stored in a separate data discovery repository 76. Files that require special processing may be exported to a grid computer infrastructure 77. At any time, files or statistical results of the data discovery process may be sent to a document production device 78 for printing and/or production on a media (e.g., disk, CD, etc.). Alternatively, files or statistical results of the data discovery process may be sent to one or more external storage devices.

Those skilled in the art of polarization measurement and polarization calculus will realize that it is possible to skip the intermediate step of calculating a Mueller matrix and construct a set of measurements and algorithm for data reduction which bypasses the Mueller matrix and calculates any of these parameters or parameters substantially similar by means which produce the same end result. These algorithms are formulated here in terms of Mueller matrix elements because this is the standard and most widely understood method for describing polarization elements with some depolarization but the Mueller matrix is not the only method.

Figure 8:
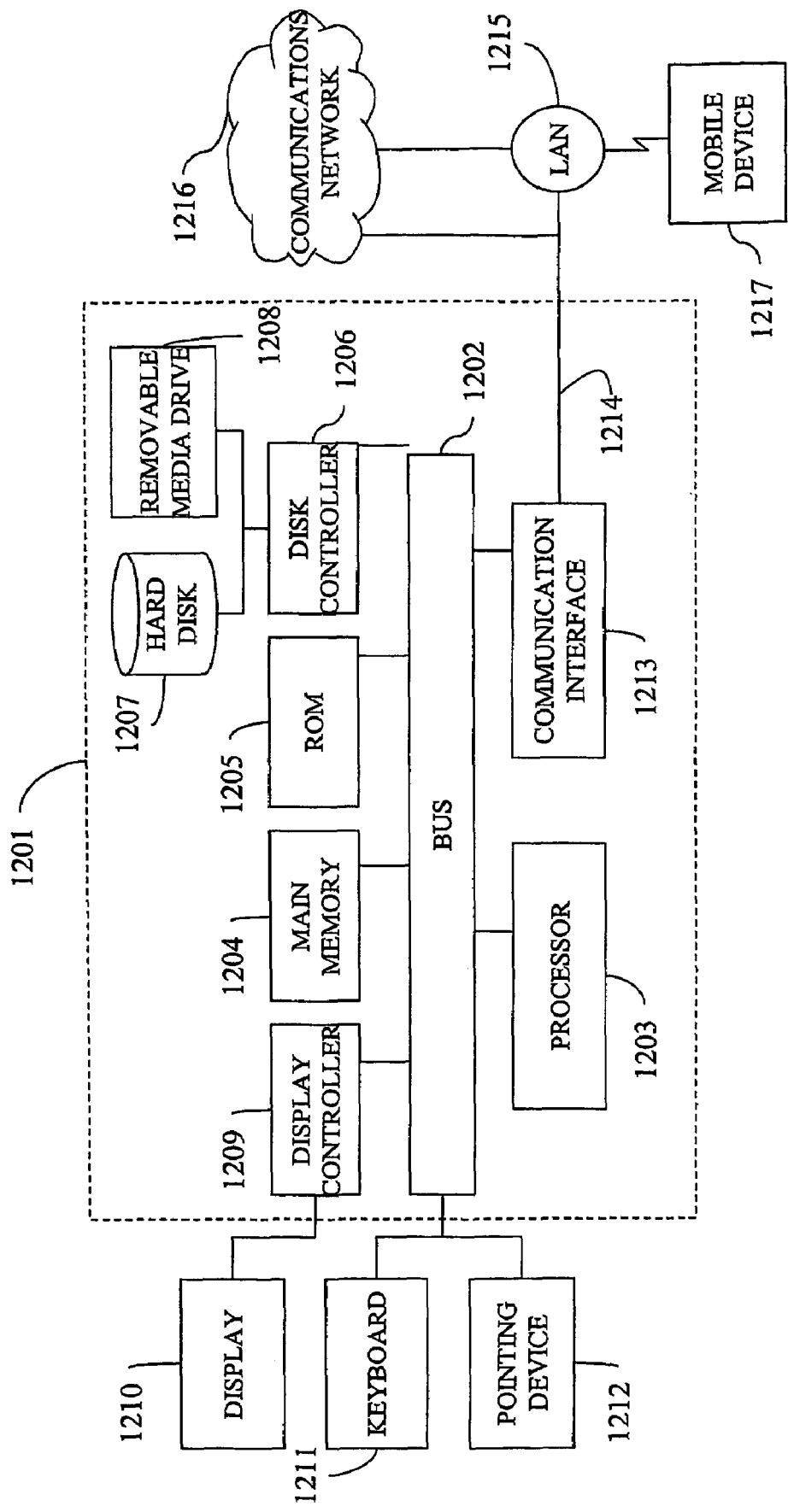
FIG. 8 is a block diagram of a computer associated with the present invention.

FIG. 8 is a block diagram of a computer system 1201 upon which an embodiment of the present invention may be implemented. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The present invention includes a user-friendly interface that allows individuals of varying skill levels to perform the previously described calculations and analysis.

Numerous modifications and variations of the present invention are possible in light of the above teachings. It is therefore to be understood that within the scope of the appended claims, the invention may be practiced otherwise than as specifically described herein.

REFERENCES

Chipman, R. A., "Polarimetry," in Handbook of Optics, Vol. II, McGraw Hill, New York (1995).

J. J. Gil and E. Bernabeu, A depolarization criterion in Mueller matrices, Opt. Acta, 32, 259-261 (1985).

Gil, J. J. and Bernabeau, E., "Depolarization and polarization indices of an optical system," Opt. Acta, 33, 185-189 (1986).

Pezzaniti, J. L., McClain, S. C., Chipman, R. A., and Lu, S. Y., "Depolarization in liquid crystal TV's," Opt. Lett., 18, 2071-2073 (1993).

Goldstein, D., Polarized Light, Second Ed., Revised and Expanded, Marcel Dekker, New York, pp. 175-185, 2003.

Lu, S.-Y. and Chipman, R. A., "Interpretation of Mueller matrices based on polar decomposition," J. Opt. Soc. Am. A, 13, 1106-1113 (1996).

Broseau, C., Fundamentals of Polarized Light, John Wiley & Sons, NY, 1998.

Dreher A W, Reiter K, Weinreb R N, "Spatially resolved birefringence of the retinal nerve fiber layer assessed with a retinal laser ellipsometer", Appl Opt 31(19), 3730-3735 (1992).

Bueno J M, Campbell M C W, "Confocal scanning laser ophthalmolscopy improvement by use of Mueller-matrix polarimetry", Opt Lett 27(10), 830-832 (2002).

Knighton R W, Huang X R, "Linear birefringence of the central human cornea", Invest Ophthalmol Vis Sci 43(1), 82-86 (2002).

Azzam R M A, "Photopolarimetric measurement of the Mueller matrix by Fourier analysis of a single detected signal", Opt Lett 2(6), 148-150 (1978)

The invention claimed is:

1. A method for identifying features in an object, comprising:
   positioning and focusing a polarimeter onto the object;
   illuminating the object with a series of at least 16 polarization states;
   analyzing a plurality of reflected images corresponding to said at least 16 polarization states;
   obtaining a Mueller matrix from the plurality of reflected images; and
   calculating a plurality of depolarization parameters, except for the depolarization index, from the Mueller matrix as a contrast mechanism for identifying features of the illuminated object.

2. The method of claim 1, wherein said depolarization parameters comprise:
   at least one of an average degree of polarization or a weighted average degree of polarization of the illuminated object.

3. The method of claim 1, wherein said depolarization parameters comprise:
   at least one of a degree of polarization surface or a degree of polarization map of the reflected images.

4. The method of claim 1, further comprising:
   calculating at least one of a minimum and a maximum degrees of polarization of the reflected images.

5. The method of claim 4, wherein said step of calculating at least one of a minimum and a maximum degrees of polarization comprises:
   calculating both a minimum and a maximum degrees of polarization; and
   calculating a difference between said minimum and a maximum degrees of polarization.

6. The method of claim 1, further comprising:
   decomposing said Mueller matrix into a depolarization matrix and at least one of a diattentuation matrix and a retardance matrix.

7. The method of claim 6, further comprising:
   calculating a depolarization relative to a corresponding diattentuation or retardance axis.

8. The method of claim 6, further comprising:
   calculating a depolarization relative to a corresponding diattentuation or retardance off-axis.

9. The method of claim 1, further comprising: calculating a ratio of diattenuation to polarizance.

10. The method of claim 1, further comprising:
    calculating a ratio of an average magnitude of Mueller matrix rows to an average magnitude of Mueller matrix columns.

11. The method according to any one of claims 1-8 or 9-10, wherein said polarimeter comprises at least one of an optical polarimeter, an X-ray polarimeter, an IR polarimeter, or a UV polarimeter.

12. A method of retinal polarimetry, comprising:
    emitting laser light to a retina via (a) a polarizer, (b) a first liquid crystal polarization controller, (c) a non-polarizing beam splitter, (d) a rotating half-wave retarder, and (e) an objective lens, the laser light passing through (a), (b) and (c) in this order;

reflecting light from the retina to a co-polarized photodetector via the objective lens to generate reflected images, the rotating half-wave retarder, the non-polarizing beam splitter, a second liquid crystal polarization controller, and a polarizing beam splitter;

obtaining a Mueller matrix from the plurality of reflected images; and calculating a plurality of depolarization parameters, except for the depolarization index, from the Mueller matrix as a contrast mechanism for identifying features of the illuminated retina.

13. The method of claim 12, further comprising:
passing light from said polarizing beam splitter to a cross-polarized photodetector.

14. The method of claim 13, further comprising:
adjusting a light parameter by controlling the retardance of said first and second liquid crystal polarization controllers by changing a respective retardance over more than one wave of retardation.

15. The method of claim 14, further comprising:
acquiring four sets of images, wherein
a first set of images corresponds to the two liquid crystal polarization controllers being adjusted to +7/8 and +7/8 waves retardance,
a second set of images corresponds to the two liquid crystal polarization controllers being adjusted to +7/8 and +9/8 waves retardance,
a third set of images corresponds to the two liquid crystal polarization controllers being adjusted to +9/8 and +9/8 waves, and
a fourth set of images corresponds to the two liquid crystal polarization controllers being adjusted to +9/8 and +7/8 waves.

16. A method of retinal polarimetry, comprising:
illuminating a retina with polarized light via a probe inserted into the eye;
producing a depolarization parameter and one of a retardance and a diattenuation parameter;
collecting light reflected off the retina with a receiver located outside of the eye or inside of the eye;
analyzing the reflected light with a polarization state analyzer;
obtaining a Mueller matrix image from the reflected light; and
analyzing said Mueller matrix by calculating a plurality of depolarization parameters, except for the depolarization index, from the Mueller matrix as a contrast mechanism for use in identifying features of the retina.

17. The method of claim 2, further comprising:
generating a polarization image with at least one of the average degree of polarization or the weighted average degree of polarization of the reflected images to detect a structure in the illuminated object.

18. The method of claim 16, further comprising:
generating a polarization image with at least one of an average degree of polarization or a weighted average degree of polarization of the reflected light to detect a structure in the retina.

19. The method of claim 11, wherein the polarimeter is a retinal polarimeter.

* * * * *